(12) United States Patent
Berrettini et al.

(10) Patent No.: US 7,736,852 B2
(45) Date of Patent: Jun. 15, 2010

(54) METHODS AND COMPOSITIONS FOR TREATING AND DIAGNOSING MOOD DISORDERS, SCHIZOPHRENIA, AND NEURO-PSYCHIATRIC DISORDERS

(75) Inventors: Wade Berrettini, Haverford, PA (US); Falk Lohoff, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 220 days.

(21) Appl. No.: 11/299,311

(22) Filed: Dec. 12, 2005

(65) Prior Publication Data

US 2006/0127933 A1    Jun. 15, 2006

Related U.S. Application Data

(60) Provisional application No. 60/668,095, filed on Apr. 5, 2005, provisional application No. 60/635,159, filed on Dec. 11, 2004.

(51) Int. Cl.
*C07H 21/04* (2006.01)
*C12Q 1/68* (2006.01)

(52) U.S. Cl. .................. 435/6; 435/91.1; 435/91.2; 536/23.1; 536/24.3

(58) Field of Classification Search .................. None
See application file for complete search history.

(56) References Cited

U.S. PATENT DOCUMENTS

2003/0092019 A1* 5/2003 Meyer et al. .................. 435/6

OTHER PUBLICATIONS

Lohoff et al. (Neuropsychopharmacology, vol. 31, pp. 2739-2747, 2006).*
Richards et al. (Behavioral and Brain Functions, vol. 2, No. 39, Nov. 30, 2006).*
Chen et al. (Schizophrenia research, vol. 90, pp. 363-365, 2007).*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Thisted (May 1998).*
Bly M. "Mutation in the vesicular monoamine gene, SLC18A1, associated with schizophrenia." Schizophr Res. Oct. 15, 2005:78(2-3):337-8.
Hansson SR, et al "Ontogeny of vesicular monoamine Ontogeny of vesicular monoamine transporter mRNAs VMAT1 and VMAT2. II. Expression in neural crest derivatives and their target sites in the rat" Brain Res Dev Brain Res. Sep. 10, 1998;110(1):159-74. PMID: 9733958.
Hansson SR, el al "Ontogeny of vesicular monoamine transporter mRNAs VMAT1 and VMAT2. I. The developing rat central nervous system" Brain Res Dev Brain Res. Sep. 10, 1998;110(1):135-58.
Treat et al., in Liposomes in the Therapy of Infectious Disease and Cancer, Lopez- Berestein and Fidler (eds.), Liss, New York, pp. 353-365 (1989).
Nurnberger J et al "Diagnostic interview for genetic studies. Rationale, unique features, and training. NIMH Genetics Initiative." Arch Gen Psychiatry 51(11): 849-59, 1994.
Langer, Science 249:1527-1533 (1990).
Lopez-Berestein et al., in Liposomes in the Therapy of Infectious Disease and Cancer, Lopez- Berestein and Fidler (eds.), Liss, New York, pp. 317-327 (1989).

* cited by examiner

*Primary Examiner*—Jeanine A Goldberg
(74) *Attorney, Agent, or Firm*—Mark S. Cohen; Pearl Cohen Zedek Latzer, LLP

(57) ABSTRACT

This invention provides: methods of determining a predisposition or susceptibility of a subject to a mood disorder, a schizophrenia, or a neuro-psychiatric disease or disorder, comprising detecting a presence of a polymorphism in a vesicular monoamine transporter 1 (VMAT1) gene or a haplotype comprising the polymorphism, and methods of treating a mood disorder, a schizophrenia, or a neuro-psychiatric disease or disorder in a subject, comprising contacting the subject with a composition that encodes a VMAT protein or modulates an expression or activity of same.

12 Claims, 1 Drawing Sheet

SEQUENCE LISTING

```
<160> NUMBER OF SEQ ID NOS: 20

<210> SEQ ID NO 1
<211> LENGTH: 525
<212> TYPE: PRT
<213> ORGANISM: Homo sapiens

<400> SEQUENCE: 1

Met Leu Arg Thr Ile Leu Asp Ala Pro Gln Arg Leu Leu Lys Glu Gly
1               5                   10                  15

Arg Ala Ser Arg Gln Leu Val Leu Val Val Val Phe Val Ala Leu Leu
            20                  25                  30

Leu Asp Asn Met Leu Phe Thr Val Val Val Pro Ile Val Pro Thr Phe
        35                  40                  45
```

```
Leu Tyr Asp Met Glu Phe Lys Glu Val Asn Ser Ser Leu His Leu Gly
         50                  55                  60

His Ala Gly Ser Ser Pro His Ala Leu Ala Ser Pro Ala Phe Ser Thr
 65              70                  75                      80

Ile Phe Ser Phe Phe Asn Asn Asn Thr Val Ala Val Glu Glu Ser Val
                 85                  90                  95

Pro Ser Gly Ile Ala Trp Met Asn Asp Thr Ala Ser Thr Ile Pro Pro
             100                 105                 110

Pro Ala Thr Glu Ala Ile Ser Ala His Lys Asn Asn Cys Leu Gln Gly
             115                 120                 125

Thr Gly Phe Leu Glu Glu Ile Thr Arg Val Gly Val Leu Phe Ala
     130                 135                 140

Ser Lys Ala Val Met Gln Leu Leu Val Asn Pro Phe Val Gly Pro Leu
145             150                 155                     160

Thr Asn Arg Ile Gly Tyr His Ile Pro Met Phe Ala Gly Phe Val Ile
                 165                 170                 175

Met Phe Leu Ser Thr Val Met Phe Ala Phe Ser Gly Thr Tyr Thr Leu
             180                 185                 190

Leu Phe Val Ala Arg Thr Leu Gln Gly Ile Gly Ser Ser Phe Ser Ser
         195                 200                 205

Val Ala Gly Leu Gly Met Leu Ala Ser Val Tyr Thr Asp Asp His Glu
         210                 215                 220

Arg Gly Arg Ala Met Gly Thr Ala Leu Gly Gly Leu Ala Leu Gly Leu
225             230                 235                     240

Leu Val Gly Ala Pro Phe Gly Ser Val Met Tyr Glu Phe Val Gly Lys
                 245                 250                 255

Ser Ala Pro Phe Leu Ile Leu Ala Phe Leu Ala Leu Asp Gly Ala
             260                 265                 270

Leu Gln Leu Cys Ile Leu Gln Pro Ser Lys Val Ser Pro Glu Ser Ala
         275                 280                 285

Lys Gly Thr Pro Leu Phe Met Leu Leu Lys Asp Pro Tyr Ile Leu Val
    290                  295                 300

Ala Ala Gly Ser Ile Cys Phe Ala Asn Met Gly Val Ala Ile Leu Glu
305             310                 315                     320

Pro Thr Leu Pro Ile Trp Met Met Gln Thr Met Cys Ser Pro Lys Trp
                 325                 330                 335

Gln Leu Gly Leu Ala Phe Leu Pro Ala Ser Val Ser Tyr Leu Ile Gly
             340                 345                 350

Thr Asn Leu Phe Gly Val Leu Ala Asn Lys Met Gly Arg Trp Leu Cys
         355                 360                 365

Ser Leu Ile Gly Met Leu Val Val Gly Thr Ser Leu Leu Cys Val Pro
    370                 375                 380

Leu Ala His Asn Ile Phe Gly Leu Ile Gly Pro Asn Ala Gly Leu Gly
385             390                 395                     400

Leu Ala Ile Gly Met Val Asp Ser Ser Met Met Pro Ile Met Gly His
                 405                 410                 415

Leu Val Asp Leu Arg His Thr Ser Val Tyr Gly Ser Val Tyr Ala Ile
             420                 425                 430

Ala Asp Val Ala Phe Cys Met Gly Phe Ala Ile Gly Pro Ser Thr Gly
         435                 440                 445

Gly Ala Ile Val Lys Ala Ile Gly Phe Pro Trp Leu Met Val Ile Thr
    450                 455                 460
```

```
Gly Val Ile Asn Ile Val Tyr Ala Pro Leu Cys Tyr Tyr Leu Arg Ser
465                 470                 475                 480

Pro Pro Ala Lys Glu Glu Lys Leu Ala Ile Leu Ser Gln Asp Cys Pro
                485                 490                 495

Met Glu Thr Arg Met Tyr Ala Thr Gln Lys Pro Thr Lys Glu Phe Pro
            500                 505                 510

Leu Gly Glu Asp Ser Asp Glu Glu Pro Asp His Glu Glu
        515                 520                 525

<210> SEQ ID NO 2
<211> LENGTH: 51
<212> TYPE: DNA
<213> ORGANISM: Homo sapiens

<400> SEQUENCE: 2
agcaaacaga accccgaccc gggtaatctc ttcctccaag aaacctgtgc c        51

<210> SEQ ID NO 3
<211> LENGTH: 51
<212> TYPE: DNA
<213> ORGANISM: Homo sapiens

<400> SEQUENCE: 3
agtgtcattc atccatgcta ttccactagg tacgctttct tcaacagcca c        51

<210> SEQ ID NO 4
<211> LENGTH: 51
<212> TYPE: DNA
<213> ORGANISM: Homo sapiens

<400> SEQUENCE: 4
aaccgctggg gagcatccag aatgggccgg agcatggtga tggccggact g        51

<210> SEQ ID NO 5
<211> LENGTH: 51
<212> TYPE: DNA
<213> ORGANISM: Homo sapiens

<400> SEQUENCE: 5
cttggaggaa gagactaccc gggtcagggt tctgtttgct tcaaaggctg t        51

<210> SEQ ID NO 6
<211> LENGTH: 51
<212> TYPE: DNA
<213> ORGANISM: Homo sapiens

<400> SEQUENCE: 6
tcctctggct cacaatattt ttggtctcat tggccccaat gcagggcttg g        51

<210> SEQ ID NO 7
<211> LENGTH: 51
<212> TYPE: DNA
<213> ORGANISM: Homo sapiens

<400> SEQUENCE: 7
tttatgaaaa agcaaataca ctttacgagc aagagcagtg cagagatttc c        51

<210> SEQ ID NO 8
<211> LENGTH: 51
<212> TYPE: DNA
<213> ORGANISM: Homo sapiens

<400> SEQUENCE: 8
```

-continued tattcatcca atttctcttg aactacatag tattttgatg ctcattttag c    51

<210> SEQ ID NO 9
<211> LENGTH: 51
<212> TYPE: DNA
<213> ORGANISM: Homo sapiens

<400> SEQUENCE: 9
aacaatgtca cattcacccc ctcctattag gaaatctaca atcaggaggg a    51

<210> SEQ ID NO 10
<211> LENGTH: 51
<212> TYPE: DNA
<213> ORGANISM: Homo sapiens

<400> SEQUENCE: 10
tccctcctga ttgtagattt cctaacagga ggggtgtaat gtgacattgt t    51

<210> SEQ ID NO 11
<211> LENGTH: 51
<212> TYPE: DNA
<213> ORGANISM: Homo sapiens

<400> SEQUENCE: 11
attagaaaca tttagctgat cctggataga gtatttgtct ttctctttct t    51

<210> SEQ ID NO 12
<211> LENGTH: 51
<212> TYPE: DNA
<213> ORGANISM: Homo sapiens

<400> SEQUENCE: 12
tttctccggg ccaaataata tctataaccc aattacatgt accctgggct g    51

<210> SEQ ID NO 13
<211> LENGTH: 51
<212> TYPE: DNA
<213> ORGANISM: Homo sapiens

<400> SEQUENCE: 13
gggccaaaat tctcatttcc agaaaggata gcctaggtgg agtgtatatc t    51

<210> SEQ ID NO 14
<211> LENGTH: 51
<212> TYPE: DNA
<213> ORGANISM: Homo sapiens

<400> SEQUENCE: 14
ccaagccctg cattggggcc aatgacacca aaaatattgt gagccagagg a    51

<210> SEQ ID NO 15
<211> LENGTH: 51
<212> TYPE: DNA
<213> ORGANISM: Homo sapiens

<400> SEQUENCE: 15
gttagtacca ccccgcctct cctcccccat ttagtccatt tgctttgtct g    51

<210> SEQ ID NO 16
<211> LENGTH: 51
<212> TYPE: DNA
<213> ORGANISM: Homo sapiens

```
<400> SEQUENCE: 16
catacatcat cctcctgcac tctcacactt tctcatggaa aagaatctat a         51

<210> SEQ ID NO 17
<211> LENGTH: 51
<212> TYPE: DNA
<213> ORGANISM: Homo sapiens

<400> SEQUENCE: 17
aacatattcc agccatggtt cctgccttca cgtgaccatc aacaaggtca g         51

<210> SEQ ID NO 18
<211> LENGTH: 51
<212> TYPE: DNA
<213> ORGANISM: Homo sapiens

<400> SEQUENCE: 18
gacttcccaa caaactcgta cattacactt ccaaagggag ctcccactgg a         51

<210> SEQ ID NO 19
<211> LENGTH: 51
<212> TYPE: DNA
<213> ORGANISM: Homo sapiens

<400> SEQUENCE: 19
gataacaaag ccagcaaaca tggggatatg atatccaatc ctaaaaggga a         51

<210> SEQ ID NO 20
<211> LENGTH: 51
<212> TYPE: DNA
<213> ORGANISM: Homo sapiens

<400> SEQUENCE: 20
cacggtgttg ttgttgaaga aggagaagat ggtggaaaag gcaggagagg c         51
```

METHODS AND COMPOSITIONS FOR TREATING AND DIAGNOSING MOOD DISORDERS, SCHIZOPHRENIA, AND NEURO-PSYCHIATRIC DISORDERS

CROSS REFERENCE TO RELATED APPLICATIONS

This application claims priority of U.S. Provisional Application Ser. No. 60/668,095, filed Apr. 5, 2005 and U.S. Provisional Application Ser. No. 60/635,159, filed Dec. 11, 2004, which are hereby incorporated in their entirety by reference herein.

STATEMENT REGARDING FEDERALLY SPONSORED RESEARCH OR DEVELOPMENT

The invention described herein was supported in whole in or in part by grants from the National Institutes of Health (Grant Nos. MH059553, MH063876, and R25 MH060490). The Government has certain rights in this invention.

FIELD OF INVENTION

This invention provides: methods of determining a predisposition or susceptibility of a subject to a mood disorder, schizophrenia, or a neuro-psychiatric disease or disorder, comprising detecting a presence of a polymorphism in a vesicular monoamine transporter 1 (VMAT1) gene or a haplotype comprising the polymorphism, and methods of treating a mood disorder, schizophrenia, or a neuro-psychiatric disease or disorder in a subject, comprising contacting the subject with a composition that encodes a VMAT protein or modulates an expression or activity of same.

BACKGROUND OF THE INVENTION

Bipolar disorder (BPD) is a common psychiatric disorder, which affects approximately 1% of the general population and is characterized by episodes of mania and depression. Family, adoption and twin studies have shown that BPD has a genetic component. However, genetic causes have been difficult to elucidate due to the complex mode of inheritance and genetic heterogeneity.

Schizophrenia is a chronic, severe, and disabling brain disease. Approximately 1 percent of the population develops schizophrenia during their lifetime—more than 2 million Americans suffer from the illness in a given year. Although schizophrenia affects men and women with equal frequency, the disorder often appears earlier in men, usually in the late teens or early twenties, than in women, who are generally affected in the twenties to early thirties. Available treatments can relieve many symptoms, but most people with schizophrenia continue to suffer some symptoms throughout their lives; it has been estimated that no more than one in five individuals recovers completely.

Methods of treating BPD, schizophrenia, and other mood disorders and neuro-psychiatric diseases and disorders are urgently needed.

SUMMARY OF THE INVENTION

This invention provides: methods of determining a predisposition or susceptibility of a subject to a mood disorder, schizophrenia, or a neuro-psychiatric disease or disorder, comprising detecting a presence of a polymorphism in a vesicular monoamine transporter 1 (VMAT1) gene or a haplotype comprising the polymorphism, and methods of treating a mood disorder, schizophrenia, or a neuro-psychiatric disease or disorder in a subject, comprising contacting the subject with a composition that encodes a VMAT protein or modulates an expression or activity of same.

In one embodiment, the present invention provides a method of determining a predisposition or susceptibility of a subject to a mood disorder, comprising determining a genotype of the subject for a polymorphism of a VMAT1 gene, thereby determining a predisposition or susceptibility of a subject to a mood disorder. In another embodiment, the presence of an allele of the polymorphism correlates with the predisposition or susceptibility to a mood disorder.

In another embodiment, the present invention provides a method of determining a predisposition or susceptibility of a subject to schizophrenia, comprising determining a genotype of the subject for a polymorphism of a VMAT1 gene, thereby determining a predisposition or susceptibility of a subject to schizophrenia. In another embodiment, the presence of an allele of the polymorphism correlates with the predisposition or susceptibility to schizophrenia.

In another embodiment, the present invention provides a method of determining a predisposition or susceptibility of a subject to a mood disorder, comprising determining a genotype of the subject for a combination of polymorphisms of a VMAT1 gene, thereby determining a predisposition or susceptibility of a subject to a mood disorder. In another embodiment, the presence of a combination of alleles of the polymorphism correlates with the predisposition or susceptibility. In another embodiment, the combination of polymorphisms defines a haplotype.

In another embodiment, the present invention provides a method of determining a predisposition or susceptibility of a subject to schizophrenia, determining a genotype of the subject for a combination of polymorphisms of a VMAT1 gene, thereby determining a predisposition or susceptibility of a subject to schizophrenia. In another embodiment, the presence of a combination of alleles of the polymorphism correlates with the predisposition or susceptibility. In another embodiment, the combination of polymorphisms defines a haplotype.

In another embodiment, the present invention provides a method of treating a mood disorder in a subject, comprising contacting the subject with a nucleic acid encoding a VMAT protein, thereby treating a mood disorder in a subject.

In another embodiment, the present invention provides a method of treating schizophrenia in a subject, comprising contacting the subject with a nucleic acid encoding a VMAT protein, thereby treating schizophrenia in a subject In another embodiment, the present invention provides a method of treating a neuro-psychiatric disease or disorder in a subject, comprising contacting the subject with a nucleic acid encoding a VMAT protein, thereby treating a neuro-psychiatric disease or disorder in a subject

DETAILED DESCRIPTION OF THE INVENTION

Figure 1:
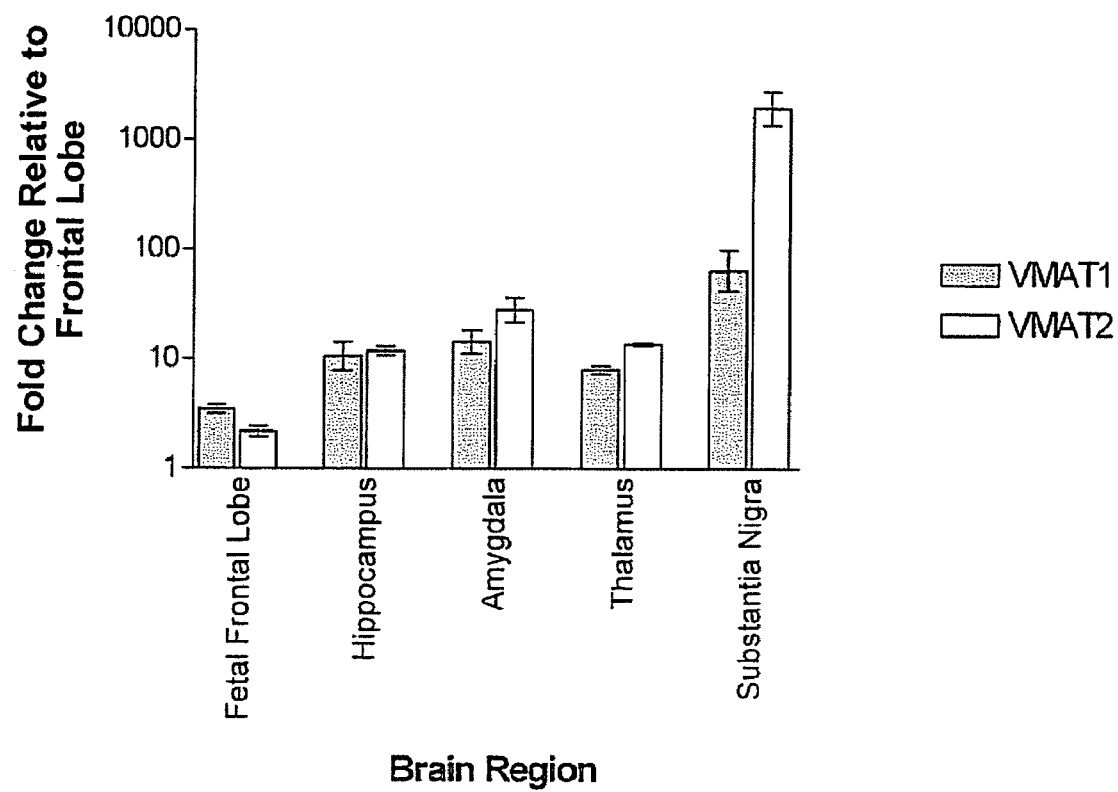
FIG. 1. Real-time quantitative PCR determination of mRNA levels for VMAT1 and VMAT2 in human brain regions. Data shown as mean±s.e.m. of three independent experiments using the comparative Ct method.

This invention provides: methods of determining a predisposition or susceptibility of a subject to a mood disorder, schizophrenia, or a neuro-psychiatric disease or disorder, comprising detecting a presence of a polymorphism in a vesicular monoamine transporter 1 (VMAT1) gene or a haplotype comprising the polymorphism, and methods of treating a mood disorder, schizophrenia, or a neuro-psychiatric disease or disorder in a subject, comprising contacting the subject with a composition that encodes a VMAT protein or modulates an expression or activity of same.

In one embodiment, the present invention provides a method of determining a predisposition or susceptibility of a subject to a mood disorder, comprising determining a genotype of the subject for a polymorphism of a VMAT1 gene, thereby determining a predisposition or susceptibility of a subject to a mood disorder. In another embodiment, the presence of an allele of the polymorphism correlates with the predisposition or susceptibility to a mood disorder. As provided herein (Example 1), polymorphisms of VMAT1 correlate with predisposition to development of bipolar disorder (BPD) and other mood disorders, and susceptibility to development of such disorders.

In one embodiment, the present invention provides a method of determining a predisposition or susceptibility of a subject to a mood disorder, comprising testing a subject for an allele of a polymorphism of a VMAT1 gene, thereby determining a predisposition or susceptibility of a subject to a mood disorder. In another embodiment, the presence of the allele correlates with the predisposition or susceptibility.

In another embodiment, the present invention provides a method of determining a predisposition or susceptibility of a subject to schizophrenia, comprising determining a genotype of the subject for a polymorphism of a VMAT1 gene, thereby determining a predisposition or susceptibility of a subject to schizophrenia. In another embodiment, the presence of an allele of the polymorphism correlates with the predisposition or susceptibility to schizophrenia. As provided herein (Example 3), polymorphisms of VMAT1 correlate with predisposition to development of schizophrenia, and susceptibility to development of same.

In another embodiment, the present invention provides a method of determining a predisposition or susceptibility of a subject to schizophrenia, comprising testing a subject for an allele of a polymorphism of a VMAT1 gene, thereby determining a predisposition or susceptibility of a subject to schizophrenia. In another embodiment, the presence of the allele of the polymorphism correlates with the predisposition or susceptibility.

In another embodiment, the present invention provides a method of determining a predisposition or susceptibility of a subject to a mood disorder, comprising determining a genotype of the subject for a combination of polymorphisms of a VMAT1 gene, thereby determining a predisposition or susceptibility of a subject to a mood disorder. In another embodiment, the presence of a combination of alleles of the polymorphism correlates with the predisposition or susceptibility. In another embodiment, the combination of polymorphisms defines a haplotype. As provided herein (Example 2), VMAT1 haplotypes correlate with predisposition to BPD and other mood disorders, and susceptibility to development of such disorders.

In another embodiment, the present invention provides a method of determining a predisposition or susceptibility of a subject to a mood disorder, comprising testing the subject for the presence of a haplotype, wherein the haplotype comprises a polymorphism of a VMAT1 gene, thereby determining a predisposition or susceptibility of a subject to a mood disorder. In another embodiment, the presence of the haplotype correlates with the predisposition or susceptibility.

In another embodiment, the present invention provides a method of determining a predisposition or susceptibility of a subject to schizophrenia, determining a genotype of the subject for a combination of polymorphisms of a VMAT1 gene, thereby determining a predisposition or susceptibility of a subject to schizophrenia. In another embodiment, the presence of a combination of alleles of the polymorphism correlates with the predisposition or susceptibility. In another embodiment, the combination of polymorphisms defines a haplotype. As provided herein (Example 3), VMAT1 haplotypes correlate with predisposition to schizophrenia, and susceptibility to development of same.

In another embodiment, the present invention provides a method of determining a predisposition or susceptibility of a subject to schizophrenia, comprising testing the subject for the presence of a haplotype, wherein the haplotype comprises a polymorphism of a VMAT1 gene, thereby determining a predisposition or susceptibility of a subject to schizophrenia. In another embodiment the presence of the haplotype correlates with the predisposition or susceptibility.

In another embodiment, the present invention provides a method of determining a predisposition or susceptibility of a subject to a neuro-psychiatric disease or disorder, comprising determining a genotype of the subject for a combination of polymorphisms of a VMAT1 gene, thereby determining a predisposition or susceptibility of a subject to a neuro-psychiatric disease or disorder. In another embodiment, the presence of a combination of alleles of the polymorphism correlates with the predisposition or susceptibility. In another embodiment, the combination of polymorphisms defines a haplotype. As provided herein, VMAT1 is expressed in the brain, and plays a role in a number of neuro-psychiatric diseases and disorders.

In another embodiment, the present invention provides a method of determining a predisposition or susceptibility of a subject to a neuro-psychiatric disease or disorder, comprising testing the subject for the presence of a haplotype, wherein the haplotype comprises a polymorphism of a VMAT1 gene, thereby determining a predisposition or susceptibility of a subject to a neuro-psychiatric disease or disorder. In another embodiment, the presence of the haplotype correlates with the predisposition or susceptibility "Genotype," in one embodiment, refers to the presence of a particular allele at a specified locus in the subject's genome. In another embodiment, "genotype" refers to the presence of 2 particular alleles on the 2 homologous loci on the homologous chromosomes of the subject. In another embodiment, "genotype" refers to a combination of alleles at several loci (e.g. several loci that form a haplotype). In another embodiment, "genotype" refers to any other definition of "genotype" used in the art. Each possibility represents a separate embodiment of the present invention.

"Predisposition," in one embodiment, refers to an increased likelihood of developing schizophrenia. In another embodiment, "predisposition" refers to an increased likelihood of currently having schizophrenia. In one embodiment, the increased likelihood is about 10% greater than the general population. In another embodiment, the likelihood is about 20% greater than the general population. In another embodiment, the likelihood is about 30% greater than the general population. In another embodiment, the likelihood is about 40% greater than the general population. In another embodiment, the likelihood is about 50% greater than the general population. In another embodiment, the likelihood is about 60% greater than the general population. In another embodiment, the likelihood is about 80% greater than the general population. In another embodiment, the likelihood is about 2-fold greater than the general population. In another embodiment, the likelihood is about 3-fold greater than the general population. In another embodiment, the likelihood is about 5-fold greater than the general population. In another embodiment, the likelihood is about 10-fold greater than the general population. In another embodiment, the increased likelihood is more than 10-fold greater than the general population. In another embodiment, the increased likelihood is assessed relative to a subject testing negative for the polymorphism or the haplotype. In another embodiment, the increased likelihood is assessed relative to a subject in a particular subgroup of the general population. Each possibility represents a separate embodiment of the present invention.

"Correlates" refers, in one embodiment, to a negative correlation. In another embodiment, "correlates" refers to a positive correlation. In another embodiment, the correlation is manifest only in certain subpopulations, e.g. individuals of a particular type of descent or nationality, particular age groups, or individuals with an additional polymorphism or clinical correlate. Each possibility represents a separate embodiment of the present invention.

In one embodiment, the subject of methods of the present invention is a male. In another embodiment, the subject is a female. In another embodiment, the subject is an adult. In another embodiment, the subject is a child. In another embodiment, the subject is over about 25 years old. In another embodiment, the subject is over about 30 years old. In another embodiment, the subject is over about 35 years old. In another embodiment, the subject is over about 40 years old. In another embodiment, the subject is over about 50 years old. In another embodiment, the subject is over about 60 years old. In another embodiment, the subject is over about 70 years old.

In another embodiment, the subject does not currently have the mood disorder, schizophrenia, or neuro-psychiatric disease or disorder that is being tested for. In another embodiment, the subject has a family history of the mood disorder, schizophrenia, or neuro-psychiatric disease or disorder. In another embodiment, the subject has demonstrated a proclivity for the mood disorder, schizophrenia, or neuro-psychiatric disease or disorder. In another embodiment, the subject exhibits a clinical correlate of susceptibility to the mood disorder, schizophrenia, or neuro-psychiatric disease or disorder. In another embodiment, the subject is any other type of subject known in the art. Each of the above types of subject represents a separate embodiment of the present invention.

"Haplotype" refers, in one embodiment, to a group of alleles that tend to segregate together. In another embodiment, "haplotype" refers to a group of alleles whose loci are in close physical proximity. In another embodiment, "haplotype" refers to a set of closely linked alleles (genes or DNA polymorphisms) that tend to be inherited as a unit. Each type of haplotype represents a separate embodiment of the present invention.

"Close physical proximity" refers, in one embodiment, to a distance of less than 5 centimorgans. In another embodiment, the term refers to a distance of less than 4 centimorgans. In another embodiment, the distance is less than 3 centimorgans. In another embodiment, the distance is less than 2 centimorgans. In another embodiment, the distance is less than 1.5 centimorgans. In another embodiment, the distance is less than 1 centimorgans. In another embodiment, the distance is less than 0.7 centimorgans. In another embodiment, the distance is less than 0.5 centimorgans. In another embodiment, the distance is less than 0.3 centimorgans. In another embodiment, the distance is less than 0.2 centimorgans. In another embodiment, the distance is less than 0.1 centimorgans. In another embodiment, the distance is less than 0.07 centimorgans. In another embodiment, the distance is less than 0.05 centimorgans. In another embodiment, the distance is less than 0.03 centimorgans. In another embodiment, the distance is less than 0.02 centimorgans. In another embodiment, the distance is less than 0.01 centimorgans. Each possibility represents a separate embodiment of the present invention.

In one embodiment, the polymorphism detected by a method of the present invention, or present in a haplotype that is detected by a method of the present invention, is a single-nucleotide polymorphism (SNP). In another embodiment, the polymorphism is any other type of polymorphism known in the art. Each possibility represents a separate embodiment of the present invention.

In another embodiment, the polymorphism is in the coding sequence for AA 136. In another embodiment, the polymorphism is Thr136Ile. In another embodiment, the polymorphism is dbSNP rs# cluster id Rs1390938. In another embodiment, the polymorphism is an A/G polymorphism in the sequence: AGCAAACAGAACCCCGACCCGGGTAATCT CTTCCTCCAAGAAACCTGTGCC (SEQ ID No: 2; polymorphic residue underlined), or a homologous sequence thereof A polymorphism in AA 136 is detected, in another embodiment, by the Applied Biosystems® assay C8804621. Each possibility represents a separate embodiment of the present invention.

In another embodiment, the polymorphism is in the coding sequence for AA 98. In another embodiment, the polymorphism is Thr98Ser. In another embodiment, the polymorphism is dbSNP rs# cluster id rs2270637. In another embodiment, the polymorphism is a G/C polymorphism in the sequence: AGTGTCATTCATCCATGCTATTCCACTAG GTACGCTTTCTTCAACAGC CAC (SEQ ID No: 3; polymorphic residue underlined), or a homologous sequence thereof. A polymorphism in AA 98 is detected, in another embodiment, by the Applied Biosystems® assay C2716008. Each possibility represents a separate embodiment of the present invention.

In another embodiment, the polymorphism is in the coding sequence for AA 4. In another embodiment, the polymorphism is Thr4Pro. In another embodiment, the polymorphism is dbSNP rs# cluster id rs2270641. In another embodiment, the polymorphism is a G/T polymorphism in the sequence: AACCGCTGGGGAGCATCCAGAATGGGCCGGAGCA TGGTGATGGCCGGACTG (SEQ ID No: 4; polymorphic residue underlined), or a homologous sequence thereof A polymorphism in AA 4 is detected, in another embodiment, by the Applied Biosystems® assay RS2270641-161 Each possibility represents a separate embodiment of the present invention.

In another embodiment, the polymorphism is in the coding sequence for AA 11. In another embodiment, the polymorphism is Gln11Arg. In another embodiment, the polymorphism is dbSNP rs# cluster id rs17092144. In another embodiment, the polymorphism is dbSNP rs# cluster id rs17840517. In another embodiment, the polymorphism is an A/G polymorphism in the sequence: CTTGGAGGAA-GAGACTACCCGGGTCAGGGTTCTGTTTGCTTCAAA-GGCTGT (SEQ ID No: 5; polymorphic residue underlined), or a homologous sequence thereof. A polymorphism in is detected, in another embodiment, by the Applied Biosystems® assay RS17840571-114. Each possibility represents a separate embodiment of the present invention.

In another embodiment, the polymorphism is in the coding sequence for AA 392. In another embodiment, the polymorphism is Leu392Val. In another embodiment, the polymorphism is dbSNP rs# cluster id rs17092104. In another embodiment, the polymorphism is a C/G polymorphism in the sequence: TCCTCTGGCTCACAATATTTTTGGT CTCATTGGCCCCAATGCAGGGCTTGG (SEQ ID No: 6; polymorphic residue underlined), or a homologous sequence thereof. A polymorphism in AA 392 is detected, in another embodiment, by the Applied Biosystems® assay RS17092104-106. Each possibility represents a separate embodiment of the present invention.

In another embodiment, the polymorphism is a C/T polymorphism located at position −584 in the upstream untranslated region of a VMAT gene. In another embodiment, the polymorphism is dbSNP rs# cluster id rs988713. In another embodiment, the polymorphism is a C/T polymorphism in the sequence TTTATGAAAAAGCAAATACACTTTA CGAGCAAGAGCAGTGCAGAGATTTCC (SEQ ID No: 7; polymorphic residue underlined), or a homologous sequence thereof. This polymorphism is detected, in another embodiment by the Applied Biosystems® D assay C_8804626_10. Each possibility represents a separate embodiment of the present invention.

In another embodiment, the polymorphism is a C/G polymorphism in the intronic sequence: TATTCATCCAATTTCTCTTGAACTA CATAGTATTTTGATGCTCATTTTAGC (SEQ ID No: 8; polymorphic residue underlined), or a homologous sequence thereof. In another embodiment, the polymorphism is dbSNP rs# cluster id Rs3735835. The above polymorphism is detected, in another embodiment, by the Applied Biosystems® assay C2715981. Each possibility represents a separate embodiment of the present invention.

In another embodiment, the polymorphism is an A/G polymorphism in the intronic sequence: AACAATGTCACATTACACCCCTCCTATTAGGAAATCTACAATCAGGAGGG A (SEQ ID No: 9; polymorphic residue underlined), or a homologous sequence thereof.

In another embodiment, the polymorphism is a G/T polymorphism in the intronic sequence: GGGCCAAAATTCTCATTTCCAGAAA GGATAGCCTAGGTGGAGTGTATATC T (SEQ ID No: 13; polymorphic residue underlined), or a homologous sequence thereof. In another embodiment, the polymorphism is dbSNP rs# cluster id Rs2279709. The above polymorphism is detected, in another embodiment, by the Applied Biosystems® assay C2716007. Each possibility represents a separate embodiment of the present invention.

In another embodiment, the polymorphism is a C/G polymorphism in the sequence: CCAAGCCCTGCATTGGGGCCAATGACACCAAAAATATTGTGAGCCAGAGGA (SEQ ID No: 14; polymorphic residue underlined), or a homologous sequence thereof. The above polymorphism is detected, in another embodiment, by the Applied Biosystems® assay C_2715953_10 Each possibility represents a separate embodiment of the present invention.

In another embodiment, the polymorphism is a C/T polymorphism in the intronic sequence: GTTAGTACCACCCCGCCTCTCCTCC CCCATTTAGTCCATTTGCTTTGTCTG (SEQ ID No: 15; polymorphic residue underlined), or a homologous sequence thereof. In another embodiment, the polymorphism is dbSNP rs# cluster id rs1018079. The above polymorphism is detected, in another embodiment, by the Applied Biosystems® assay C_8804594_10. Each possibility represents a separate embodiment of the present invention.

In another embodiment, the polymorphism is a C/G polymorphism in the intronic sequence: CATACATCATCCTCCTGCACTCTCA CACTTTCTCATGGAAAAGAATCTATA (SEQ ID No: 16; polymorphic residue underlined), or a homologous sequence thereof. In another embodiment, the polymorphism is dbSNP rs# cluster id rs903997. The above polymorphism is detected, in another embodiment, by the Applied Biosystems® assay C_8804602_10. Each possibility represents a separate embodiment of the present invention In another embodiment, the polymorphism is a C/G polymorphism in the intronic sequence: AACATATTCCAGCCATGGTTCCTGC CTTCACGTGACCATCAACAAGGTCAG (SEQ ID No: 17; polymorphic residue underlined), or a homologous sequence thereof. In another embodiment, the polymorphism is dbSNP rs# cluster id rs3779671. The above polymorphism is detected, in another embodiment, by the Applied Biosystems® assay C_22273041_10. Each possibility represents a separate embodiment of the present invention.

In another embodiment, the polymorphism is a C/T polymorphism in the intronic sequence: GACTTCCCAACAAACTCGTACATTA CACTTCCAAAGGGAGCTCCCACTGGA (SEQ ID No: 18; polymorphic residue underlined), or a homologous sequence thereof. The above polymorphism is detected, in another embodiment, by the Applied Biosystems® assay C_25603200_10. Each possibility represents a separate embodiment of the present invention.

In another embodiment, the polymorphism is an A/G polymorphism in the intronic sequence: GATAACAAAGCCAGCAAACATGGGG ATATGATATCCAATCCTAAAAGGGAA (SEQ ID No: 19; polymorphic residue underlined), or a homologous sequence thereof. The above polymorphism is detected, in another embodiment, by the Applied Biosystems® assay C_25603220_10. Each possibility represents a separate embodiment of the present invention.

In another embodiment, the polymorphism is an A/C polymorphism in the intronic sequence: CACGGTGTTGTTGTTGAAGAAGGAG AAGATGTGGAAAAGGCAGGAGAGGC (SEQ ID No: 20; polymorphic residue underlined), or a homologous sequence thereof. The above polymorphism is detected, in another embodiment, by the Applied Biosystems® assay C_25603240_10. Each possibility represents a separate embodiment of the present invention.

In another embodiment, the polymorphism is a C/T polymorphism in the intronic sequence: TCCCTCCTGATTGTAGATTTCCTAACAGGAGGGGTGTAATGTGACATTGTT (SEQ ID No: 10; polymorphic residue underlined), or a homologous sequence thereof. In another embodiment, the polymorphism is dbSNP rs# cluster id rs1497020. The above polymorphism is detected, in another embodiment, by the Applied Biosystems® assay C2715947. Each possibility represents a separate embodiment of the present invention.

In another embodiment, the polymorphism is an A/G polymorphism in the sequence: ATTAGAAACATTTAGCTGATCCTGGATAGAGTATTTGTCTTTCTCTTTCTT (SEQ ID No: 11; polymorphic residue underlined), or a homologous sequence thereof. In another embodiment, the polymorphism is dbSNP rs# cluster id Rs6586897. The above polymorphism is detected, in another embodiment, by the Applied Biosystems® assay C2716000. Each possibility represents a separate embodiment of the present invention.

In another embodiment, the polymorphism is an A/T polymorphism in the sequence: TTTCTCCGGGCCAAATAATATCTAT AACCCAATTACATGTACCCTGGGCTG (SEQ ID No: 12; polymorphic residue underlined), or a homologous sequence thereof. In another embodiment, the polymorphism is dbSNP rs# cluster id Rs7820517. The above polymorphism is detected, in another embodiment, by the Applied Biosystems® assay C2716022. Each possibility represents a separate embodiment of the present invention.

As is well known in the art, the sequences provided herein can be either sequences from the coding strand or non-coding strand of the VMAT gene. The corresponding sequence of the coding strand can be readily derived from a non-coding strand sequence provided herein.

In another embodiment, the polymorphism is located in a coding region of the VMAT1 gene. The polymorphism can encode, in other embodiments, any AA known in the art. In another embodiment, the polymorphism is located in an exon of the VMAT1 gene. In another embodiment, the polymorphism is located in an intron of the VMAT1 gene. In another embodiment, the polymorphism is located in an upstream region of the VMAT1 gene. In another embodiment, the polymorphism is located in a promoter of the VMAT1 gene. In another embodiment, the polymorphism is located in an enhancer of the VMAT1 gene. Each location represents a separate embodiment of the present invention.

In another embodiment, the polymorphism is located in a codon that encodes amino acid (AA) 136 of a protein encoded by the VMAT1 gene. In another embodiment, the polymorphism is located in a codon that encodes AA 4 of a VMAT protein. In another embodiment, the polymorphism is located in a codon that encodes AA 98 of a VMAT protein. The numbering of AA 4, 98, and 136 are based on the following sequence:

```
MLRTILDAPQRLLKEGRASRQLVLVVVFVALLLDNMLFTVVVPIVPTFL

YDMEFKEVNSSLHLGHAGSSPHALASPAFSTIFSFFNNNTVAVEESVPS

GIAWMNDTASTIPPPATEAISAHKNNCLQGTGFLEEEITRVGVLFASK

AVMQLLVNPFVGPLTNRIGYHIPMFAGFVIMFLSTVMFAFSGTYTLLFV

ARTLQGIGSSFSSVAGLGMLASVYTDDHERGRAMGTALGGLALGLLVGA

PFGSVMYEFVGKSAPFLILAFLALLDGALQLCILQPSKVSPESAKGTPL

FMLLKDPYILVAAGSICFANMGVAILEPTLPIWMMQTMCSPKWQLGLAF

LPASVSYLIGTNLFGVLANKMGRWLCSLIGMLVVGTSLLCVPLAHNIFG

LIGPNAGLGLAIGMVDSSMMPIMGHLVDLRHTSVYGSVYAIADVAFCMG

FAIGPSTGGAIVKAIGFPWLMVITGVNIVYAPLCYYLRSPPAKEEKLA

ILSQDCPMETRMYATQKPTKEFPLGEDSDEEPDHEE  (GenBank

Accession No. NM_003053; SEQ ID No: 1).
```

In another embodiment, the polymorphism is any other non-coding polymorphism in the VMAT1 gene. In another embodiment, the polymorphism is any other intronic polymorphism in the VMAT1 gene. In another embodiment, the polymorphism is in the vicinity of the VMAT1 gene.

In another embodiment, the sequence of the VMAT gene of methods of the present invention is that disclosed in GenBank Accession No. BC009387. In another embodiment, the sequence is that disclosed in GenBank Accession No. BC006317. In another embodiment, the sequence is disclosed in GenBank Accession No. U39905. In another embodiment, the VMAT gene is referred to as "solute carrier family 18 (SCL18) member 1." In another embodiment, the VMAT gene is any gene that encodes a VMAT protein or an SCL18A protein. In another embodiment, the VMAT gene is any gene that encodes a VMAT1 protein or an SCL18A1 protein. In another embodiment, the VMAT1 gene is referred to as "SCL18A1." In another embodiment, the VMAT1 gene is a homologue of any of the VMAT1 sequences of the present invention. In another embodiment, the VMAT1 gene is a variant of any of the VMAT1 sequences of the present invention. Each possibility represents a separate embodiment of the present invention.

Related VMAT1 proteins of different sequences will, in another embodiment, have an AA residue with a different number that corresponds to AA 136, AA98, or AA4. In another embodiment, such polymorphisms fall within the scope of the present invention.

In another embodiment, variants and homologues of VMAT1 have non-coding polymorphisms (e.g. intronic polymorphisms or polymorphisms in upstream or downstream untranslated regions) that correspond in sequence to non-coding polymorphisms of the present invention, but are in different positions than those enumerated herein. In another embodiment, the non-coding polymorphisms are homologous in sequence to non-coding polymorphisms of the present invention, but are in different positions than those enumerated herein. Each possibility represents a separate embodiment of the present invention.

In another embodiment, the polymorphism detected in a method of the present invention is another polymorphism associated with a haplotype of the present invention. In another embodiment, multiple polymorphisms associated with a haplotype of the present invention affect susceptibility or predisposition to a mood disorder (e.g. BPD) or schizophrenia. In another embodiment, a combination of polymorphisms affect susceptibility or predisposition to the disorder. Thus, in another embodiment, a method of the present invention comprises detecting multiple polymorphisms. Each possibility represents a separate embodiment of the present invention.

Each VMAT1 sequence represents a separate embodiment of the present invention. Each type of polymorphism represents a separate embodiment of the present invention.

The combination of polymorphisms or haplotype that is detected by a method of the present invention comprises, in another embodiment, at least 2 polymorphisms selected from (a) a polymorphism in position −584 of the VMAT1 gene; (b) a polymorphism in codon 4 of the VMAT1 gene; (c) polymorphism in codon 98 of the VMAT1 gene; (d) a polymorphism in codon 136 of the VMAT1 gene; (e) a polymorphism in the sequence set forth in SEQ ID No: 9 or a homologous sequence thereof; and (f) a polymorphism in the sequence set forth in SEQ ID No: 8 or a homologous sequence thereof.

In another embodiment, the haplotype comprises at least 3 of the above 6 polymorphisms. In another embodiment, the haplotype comprises at least 5 of the above 6 polymorphisms. In another embodiment, the haplotype least 5 of the above 6 polymorphisms. In another embodiment, the haplotype comprises all 6 of the above polymorphisms. In another embodiment, the haplotype consists of the above 6 polymorphisms. Each possibility represents a separate embodiment of the present invention.

In another embodiment, the combination of polymorphisms or haplotype is G-Thr-Thr-Ile-A-G, as defined in Example 2. The findings of Example 2 show that this haplotype is associated with a low susceptibility to BPD. In another embodiment, the haplotype is A-Thr-Thr-Thr-A-C. In another embodiment, the haplotype is A-Thr-Ser-Thr-C-G. In another embodiment, the haplotype is A-Pro-Thr-Thr-C-C. In another embodiment, the haplotype is A-Thr-Thr-Thr-A-G. In another embodiment, the haplotype is any other haplotype that comprises a polymorphism of AA 136 of VMAT1, or a corresponding AA of a VMAT1 variant or homologue. In another embodiment, the haplotype is any other haplotype that comprises an SNP1 of VMAT1, or a corresponding location of a VMAT1 variant or homologue. In another embodiment, the haplotype is any other haplotype that comprises a polymorphism in codon 136 of VMAT1, or a corresponding location of a VMAT1 variant or homologue. Each possibility represents a separate embodiment of the present invention.

In another embodiment, the combination of polymorphisms or haplotype that is detected by a method of the present invention comprises at least 2 polymorphisms selected from (a) a polymorphism in position −584 of the VMAT1 gene; (b) polymorphism in codon 4 of the VMAT1 gene; (c) a polymorphism in codon 98 of the VMAT1 gene; (d) a polymorphism in codon 136 of the VMAT1 gene; (e) a polymorphism in the sequence set forth in SEQ ID No: 9 or a homologous sequence thereof; and (f) a polymorphism in codon 392 of the VMAT1 gene.

In another embodiment, the combination of polymorphisms or haplotype comprises at least 3 of the above 6 polymorphisms. In another embodiment, the haplotype comprises at least 4 of the above 6 polymorphisms. In another embodiment, the haplotype comprises at least 5 of the above 6 polymorphisms. In another embodiment, the haplotype comprises all 6 of the above polymorphisms. In another embodiment, the haplotype consists of the above 6 polymorphisms. Each possibility represents a separate embodiment of the present invention.

In another embodiment, the combination of polymorphisms or haplotype is 1-2-1-1-1-1, as defined in Example 3. In another embodiment, the haplotype is any other haplotype that comprises a polymorphism of AA 4 of VMAT1, or a corresponding AA of a VMAT1 variant or homologue. Each possibility represents a separate embodiment of the present invention.

In another embodiment, the combination of polymorphisms or haplotype is any other haplotype that comprises a polymorphism of VMAT1. In another embodiment, the haplotype is any other haplotype located within the VMAT1 gene. In another embodiment, the haplotype is any other haplotype located partially within the VMAT1 gene. In another embodiment, the haplotype is any other haplotype that overlaps with the VMAT1 gene. Each of the above haplotypes represents a separate embodiment of the present invention.

In another embodiment, the present invention provides a method of treating a mood disorder in a subject, comprising contacting the subject with a nucleic acid encoding a VMAT protein, thereby treating a mood disorder in a subject. In another embodiment, the VMAT protein is VMAT1 In another embodiment, the VMAT protein is any other VMAT protein known in the art. Each possibility represents a separate embodiment of the present invention.

In another embodiment, the present invention provides a method of treating schizophrenia in a subject, comprising contacting the subject with a nucleic acid encoding a VMAT protein, thereby treating schizophrenia in a subject.

In another embodiment, the present invention provides a method of treating a neuro-psychiatric disease or disorder in a subject, comprising contacting the subject with a nucleic acid encoding a VMAT protein, thereby treating a neuro-psychiatric disease or disorder in a subject.

As provided herein (Examples), protein products of VMAT1/SLC18A1 play an important role in the etiology of BPD and schizophrenia, and neuro-psychiatric diseases and disorders. Thus, providing functional VMAT1 protein to the brain or a dysfunctional region thereof, or modulation of activity or expression of VMAT proteins, has utility in treating mood disorders, e.g. BPD. In another embodiment, VMAT activity or the VMAT protein is modulated by supplying a nucleic acid that encodes VMAT. In another embodiment, the VMAT activity or protein is supplied via gene therapy. In another embodiment, any other method of modulating VMAT activity or expression is utilized. Each possibility represents a separate embodiment of the present invention.

In one embodiment, the nucleic acid utilized in methods of present invention is a ribonucleic acid (RNA) molecule. In another embodiment, the nucleic acid is a deoxyribonucleic acid (DNA) molecule. In another embodiment, the nucleic acid is an antisense RNA molecule. In one embodiment, the antisense nucleic acid molecule hybridizes to a nucleic acid encoding the VMAT1 protein. In another embodiment, the antisense nucleic acid molecule hybridizes to any other cellular RNA known in the art. Each possibility represents a separate embodiment of the present invention.

In another embodiment, the VMAT protein that is supplied by a method of the present invention is a functional VMAT protein. In another embodiment, the VMAT protein is a fully functional VMAT protein. In another embodiment, the VMAT protein is a wild-type VMAT protein. In another embodiment, the VMAT protein is an activated form (e.g. a constitutively activated form) of VMAT. In another embodiment, the VMAT protein is any other form of VMAT that is useful in supplying an activity that is missing in the disease or disorder that is being treated. Each possibility represents a separate embodiment of the present invention.

In another embodiment, the present invention provides a method of treating a mood disorder in a subject, comprising contacting the subject with a composition that modulates an expression of a VMAT1 protein, thereby treating a mood disorder in a subject. In another embodiment, the present invention provides a method of treating a mood disorder in a subject, comprising contacting the subject with a composition that modulates an activity of a VMAT1 protein, thereby treating a mood disorder in a subject.

In another embodiment, the present invention provides a method of treating schizophrenia in a subject, comprising contacting the subject with a composition that modulates an expression of a VMAT1 protein, thereby treating schizophrenia in a subject. In another embodiment, the present invention provides a method of treating schizophrenia in a subject, comprising contacting the subject with a composition that modulates an activity of a VMAT1 protein, thereby treating schizophrenia in a subject.

In another embodiment, the present invention provides a method of treating a neuro-psychiatric disease or disorder in a subject, comprising contacting the subject with a composition that modulates an expression of a VMAT1 protein, thereby treating a neuro-psychiatric disease or disorder in a subject. In another embodiment, the present invention provides a method of treating a neuro-psychiatric disease or disorder in a subject, comprising contacting the subject with a composition that modulates an activity of a VMAT1 protein, thereby treating a neuro-psychiatric disease or disorder in a subject.

Each method represents a separate embodiment of the present invention.

In another embodiment, the composition used in a method of the present invention increases the expression of the VMAT1 protein. In another embodiment, the composition decreases the expression of the VMAT1 protein. In one embodiment, the composition affects VMAT1 expression via transcriptional modulation. In another embodiment, the composition acts by modulating translation of VMAT protein. In another embodiment, the composition acts via a post-translational mechanism. Each possibility represents a separate embodiment of the present invention.

In one embodiment of methods of present invention, the composition that is administered increases the activity of the VMAT 1 protein. In another embodiment, the composition decreases the activity of the VMAT1 protein. In another embodiment, the composition modulates VMAT1 activity via interaction with VMAT1 protein. In another embodiment, the composition modulates VMAT1 activity via interaction with a component of a signaling pathway or enzymatic process in which VMAT1 is involved. In another embodiment, the composition modulates VMAT1 activity via interaction with a molecule that regulates VMAT1 activity. Each possibility represents a separate embodiment of the present invention In another embodiment, the composition administered in methods of the present invention is a nucleic acid. In another embodiment, the composition is a protein. In another embodiment, the composition is a molecule that interacts with a cell in the subject or a component thereof. The component may be, e.g., a protein, nucleic acid, enzyme, cellular membrane, cellular organelle, etc. Each possibility represents a separate embodiment of the present invention.

In one embodiment of methods of the present invention, the composition is administered to the brain. In another embodiment, the composition is administered to the central nervous system (CNS). In another embodiment, the composition is administered to the substantia nigra. In another embodiment, the composition is administered to the amygdale. In another embodiment, the composition is administered to the hippocampus. In another embodiment, the composition is administered to the thalamus. In another embodiment, the composition is administered to the frontal lobe. In another embodiment, the composition is administered to another region of the brain.

In another embodiment, the composition is administered to the subject systemically. In another embodiment, the composition is administered to the subject is such as manner that it is targeted to the CNS. In another embodiment, the composition is administered to the blood-brain barrier.

In another embodiment, the phrase "contacting a cell" or "contacting a population" refers to a method of exposure, which may be direct or indirect. In one method such contact comprises direct injection of the cell through any means well known in the art, such as microinjection. It is also envisaged, in another embodiment, that supply to the cell is indirect, such as via provision in a culture medium that surrounds the cell, or administration to a subject, via any route well mown in the art, and as described herein.

Each type of contacting or administration represents a separate embodiment of the present invention.

In another embodiment, the present invention provides a kit for determining a predisposition or susceptibility of a subject to a mood disorder, wherein the kit comprises a primer useful for determining a genotype of the subject for a polymorphism of a VMAT1 gene and instructions for use thereof.

In another embodiment, the present invention provides a kit for determining a predisposition or susceptibility of a subject to schizophrenia, wherein the kit comprises a primer useful for determining a genotype of the subject for a polymorphism of a VMAT1 gene and instructions for use thereof.

In another embodiment, the present invention provides a kit for determining a predisposition or susceptibility of a subject to a neuro-psychiatric disease or disorder, wherein the kit comprises a primer useful for determining a genotype of the subject for a polymorphism of a VMAT1 gene and instructions for use thereof.

In another embodiment, the present invention provides a kit for treating a mood disorder in a subject, wherein the kit comprises a nucleic acid encoding a VMAT protein and instructions for use thereof. In another embodiment, the kit comprises a composition that modulates an expression of a VMAT1 protein. In another embodiment, the kit comprises a composition that modulates an activity of a VMAT1 protein. Each possibility represents a separate embodiment of the present invention.

In another embodiment, the present invention provides a kit for treating schizophrenia in a subject, wherein the kit comprises a nucleic acid encoding a VMAT protein and instructions for use thereof. In another embodiment, the kit comprises a composition that modulates an expression of a VMAT1 protein. In another embodiment, the kit comprises a composition that modulates an activity of a VMAT1 protein. Each possibility represents a separate embodiment of the present invention.

In another embodiment, the present invention provides a kit for treating a neuro-psychiatric disease or disorder in a subject, wherein the kit comprises a nucleic acid encoding a VMAT protein and instructions for use thereof. In another embodiment, the kit comprises a composition that modulates an expression of a VMAT1 protein. In another embodiment, the kit comprises a composition that modulates an activity of a VMAT1 protein. Each possibility represents a separate embodiment of the present invention.

In another embodiment, a kit of the present invention comprises a reagent or apparatus useful in performing a method of the present invention. In another embodiment, the kit is useful for performing a method of the present invention. Each possibility represents a separate embodiment of the present invention.

The mood disorder referred to in methods and compositions of the present invention is, in one embodiment, a BPD. In another embodiment, the mood disorder is BPD1. In another embodiment, the mood disorder is a manic-depressive disorder. In another embodiment, the mood disorder is a unipolar depression. In another embodiment, the mood disorder is any other type of mood disorder known in the art. Each possibility represents a separate embodiment of the present invention.

The schizophrenia treated by a method of the present invention is, in one embodiment, catatonic schizophrenia. In another embodiment, the schizophrenia is paranoid schizophrenia. In another embodiment, the schizophrenia is disorganized schizophrenia. In another embodiment, the schizophrenia is undifferentiated schizophrenia. In another embodiment, the schizophrenia is residual schizophrenia. In another embodiment, the schizophrenia is negative or deficit schizophrenia. In another embodiment, the schizophrenia is any other type of schizophrenia known in the art. Each possibility represents a separate embodiment of the present invention.

The neuro-psychiatric disease or disorder treated by a method of the present invention is, in one embodiment, a substance abuse disorder. In another embodiment, the neuro-psychiatric disease or disorder is a substance dependence disorder. Each possibility represents a separate embodiment of the present invention.

In another embodiment, the substance whose abuse/dependency is treated is cocaine. In another embodiment, the substance is alcohol. In another embodiment, the substance is nicotine. In another embodiment, the substance is a benzodiazepine (e.g. Valium®, Ativan®, or Xanax®). In another embodiment, the substance is an opiate or narcotic (e.g. heroin or morphine). In another embodiment, the substance is a stimulant (e.g. an amphetamine, dextroamphetamine, methamphetamine, or methylphenidate). In another embodiment, the substance is a barbiturate (e.g. amobarbital, pentobarbital, secobarbital), chloral hydrate, or paraldehyde). In another embodiment, the substance is a hallucinogen (e.g. LSD, mescaline, psilocybin, or phencyclidine). In another embodiment, the substance is tetrahydrocannabinol (THC). In another embodiment, the substance is any other addictive substance known in the art. Each possibility represents a separate embodiment of the present invention.

In another embodiment, the neuro-psychiatric disease or disorder is a cognitive dysfunction. In one embodiment, the cognitive dysfunction is a dyslexia. In another embodiment, the cognitive dysfunction comprises a lack of attention. In another embodiment, the cognitive dysfunction comprises a lack of alertness. In another embodiment, the cognitive dysfunction comprises a lack of concentration. In another embodiment, the cognitive dysfunction comprises a lack of focus. In another embodiment, the cognitive dysfunction comprises minimal cognitive impairment. In another embodiment, the cognitive dysfunction comprises age-related memory impairment. Each possibility represents a separate embodiment of the present invention.

In another embodiment, the disease or disorder is an emotional disorder. In one embodiment, the emotional disorder comprises mania. In another embodiment, the emotional disorder comprises depression. In another embodiment, the emotional disorder comprises stress. In another embodiment, the emotional disorder comprises panic. In another embodiment, the emotional disorder comprises anxiety. In another embodiment, the emotional disorder comprises dysthymia. In another embodiment, the emotional disorder comprises psychosis. In another embodiment, the emotional disorder comprises anxiety. In another embodiment, the emotional disorder comprises a seasonal effective disorder. In another embodiment, the emotional disorder comprises a bipolar disorder.

In another embodiment, the disease or disorder is a depression. In one embodiment, the depression is an endogenous depression. In another embodiment, the depression is a major depressive disorder. In another embodiment, the depression is depression with anxiety. In another embodiment, the depression is bipolar depression. Each type of depression represents a separate embodiment of the present invention.

In another embodiment, the disease or disorder is selected from the group consisting of ataxia and Friedreich's ataxia. In another embodiment, the disease or disorder of the present invention excludes epilepsy, seizures, convulsions, and the like.

In another embodiment, the disease or disorder is a movement disorder. The movement disorder comprises, in one embodiment, a tardive dyskinesia. In another embodiment, the movement disorder comprises a dystonia. In another embodiment, the movement disorder comprises a Tourette's syndrome. In another embodiment, the movement disorder is any other movement disorder known in the art.

In another embodiment, the disease or disorder is a behavioral syndrome. In another embodiment, the disease or disorder is a neurological syndrome. In another embodiment, the behavioral syndrome or neurological syndrome follows brain trauma. In another embodiment, the behavioral syndrome or neurological syndrome follows spinal cord injury. In another embodiment, the behavioral syndrome or neurological syndrome follows anoxia.

In another embodiment, the disease or disorder is a peripheral nervous system disorder. In one embodiment, the peripheral nervous system disorder is a neuromuscular disorder. In another embodiment, the peripheral nervous system disorder is any other peripheral nervous system disorder known in the art. In another embodiment, the neuromuscular disorder is myasthenia gravis. In another embodiment, the neuromuscular disorder is post-polio syndrome. In another embodiment, the neuromuscular disorder is a muscular dystrophy.

Each disease or disorder represents a separate embodiment of the present invention.

In one embodiment, a treatment protocol of the present invention is therapeutic. In another, embodiment, the protocol is prophylactic. Each possibility represents a separate embodiment of the present invention.

In one embodiment of methods of the present invention, the step of detecting the polymorphism or haplotype comprises sequencing the VMAT1 gene. In another embodiment, the step of detecting comprises polymerase chain reaction (PCR). In another embodiment, the step of detecting comprises restriction enzyme digestion of a nucleic acid molecule. In another embodiment, the step of detecting comprises electrophoresis. In another embodiment, the step of detecting comprises hybridization of a nucleic acid molecule to a probe. In another embodiment, the step of detecting comprises a cloning of polymorphisms (COP) procedure. In another embodiment, the step of detecting comprises DNA amplification fingerprinting (DAF). In another embodiment, the step of detecting comprises any other method of detecting a polymorphism that is known in the art. Methods of detecting polymorphisms are well known in the art, and are described, for example, in *Polymophism Detection and Analysis*, Burczak and Mardis, eds, © Biotechniques Press, 2000. Each detection method represents a separate embodiment of the present invention In another embodiment, the present invention provides a method for determining the suitability of a particular therapeutic regimen (e.g. anti-schizophrenic medication) for a subject, comprising testing the subject by a method of the present invention, whereby the presence of a polymorphism or haplotype that correlates with schizophrenia or its absence indicates the suitability of the therapeutic regimen.

Methods for determining a genotype of a subject are well known in the art, and include, e.g. a genotyping assay with sequence-specific primers (Examples). In another embodiment, the method comprises a polymerase chain reaction. In another embodiment, the method is any other method known in the art. Each possibility represents a separate embodiment of the present invention.

Methods of the present invention of determining a predisposition or susceptibility of a subject to schizophrenia, mood disorder, or neuro-psychiatric disease or disorder are used, in another embodiment, to identify at-risk individuals for clinical follow-up. In another embodiment, the methods are used to identify individuals that should be treated with prophylactic medication. In another embodiment, the methods are used to identify individuals that are likely to respond to particular psychiatric medications. In another embodiment, the methods are used for any other appropriate screening application known in the art. Each possibility represents a separate embodiment of the present invention.

The terms "homology," "homologous," etc, when in reference to any protein or peptide, refer in one embodiment, to a percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art.

In another embodiment, the term "homology," when in reference to any nucleic acid sequence similarly indicates a percentage of nucleotides in a candidate sequence that are identical with the nucleotides of a corresponding native nucleic acid sequence.

Homology is, in one embodiment, determined by computer algorithm for sequence alignment, by methods well described in the art. For example, computer algorithm analysis of nucleic acid sequence homology may include the utilization of any number of software packages available, such as, for example, the BLAST, DOMAIN, BEAUTY (BLAST Enhanced Alignment Utility), GENPEPT and TREMBL packages.

In another embodiment, "homology" refers to identity of greater than 70% to SEQ ID No 1-12 or the primer sequences disclosed herein. In another embodiment, the identity is greater than 75%. In another embodiment, the identity is greater than 80%. In another embodiment, the identity is greater than 82%. In another embodiment, the identity is greater than 85%. In another embodiment, the identity is greater than 87%. In another embodiment, the identity is greater than 90%. In another embodiment, the identity is greater than 92%. In another embodiment, the identity is greater than 95%. In another embodiment, the identity is greater than 97%. In another embodiment, the identity is greater than 98%. In another embodiment, the identity is greater than 99%. In another embodiment, "homology" refers to identity of 100%.

In another embodiment, homology is determined via determination of candidate sequence hybridization, methods of which are well described in the art (See, for example, "Nucleic Acid Hybridization" Hames, B. D., and Higgins S. J., Eds. (1985); Sambrook et al., 1989, Molecular Cloning, A Laboratory Manual, (Volumes 1-3) Cold Spring Harbor Press, N.Y.; and Ausubel et al., 1989, Current Protocols in Molecular Biology, Green Publishing Associates and Wiley Interscience, N.Y). For example methods of hybridization may be carried out under moderate to stringent conditions, to the complement of a DNA encoding a native caspase peptide. Hybridization conditions being, for example, overnight incubation at 42° C. in a solution comprising: 10-20% formamide, 5×SSC (150 mM NaCl. 15 mM trisodium citrate), 50 mM sodium phosphate (pH 7. 6), 5× Denhardt's solution, 10% dextran sulfate, and 20 µg/ml denatured, sheared salmon sperm DNA In one embodiment of the present invention, "nucleic acids" refers to a string of at least two base-sugar-phosphate combinations. The term includes, in one embodiment, DNA and RNA. "Nucleotides" refers, in one embodiment, to the monomeric units of nucleic acid polymers. RNA may be in the form of a tRNA (transfer RNA), snRNA (small nuclear RNA), rRNA (ribosomal RNA), mRNA (messenger RNA), anti-sense RNA, small inhibitory RNA (siRNA), micro RNA (mRNA) and ribozymes. The use of siRNA and mRNA has been described (Caudy A A et al, Genes & Devel 16:2491-96 as references cited therein). DNA may be in form of plasmid DNA, viral DNA, linear DNA, or chromosomal DNA or derivatives of these groups. In addition these forms of DNA and RNA may be single, double, triple, or quadruple stranded. The term also includes, in one embodiment, artificial nucleic acids that may contain other types of backbones but the same bases. Examples of artificial nucleic acids are PNAs (peptide nucleic acids), phosphorothioates, and other variants of the phosphate backbone of native nucleic acids. PNA contain peptide backbones and nucleotide bases, and are able to bind both DNA and RNA molecules. The use of phosphothiorate nucleic acids and PNA are known to those skilled in the art, and are described in, for example, Neilsen P E, Curr Opin Struct Biol 9:353-57; and Raz N K et al Biochem Biophys Res Commun. 297: 1075-84. The production and use of nucleic acids is known to those skilled in art and is described, for example, in Molecular Cloning, (2001), Sambrook and Russell, eds. and Methods in Enzymology: Guide to Molecular Cloning Techniques (1987) Berger and Kimmel, eds. Each nucleic acid derivative represents a separate embodiment of the present invention.

Protein and/or peptide homology for any amino acid sequence listed herein is determined, in one embodiment, by methods well described in the art, including immunoblot analysis, or via computer algorithm analysis of amino acid sequences, utilizing any of a number of software packages available, via established methods. Some of these packages may include the FASTA, BLAST, MPsrch or Scanps packages, and may employ the use of the Smith and Waterman algorithms, and/or global/local or BLOCKS alignments for analysis, for example. Each method of determining homology represents a separate embodiment of the present invention.

Pharmaceutical Compositions

Compositions of the present invention (e.g. nucleic acids encoding a VMAT protein, or compositions that modulate the activity or expression of VMAT) can be administered to a subject by any method known to a person skilled in the art, such as parenterally, paracancerally, transmucosally, transdermally, intramuscularly, intravenously, intradermally, subcutaneously, intraperitonealy, intraventricularly, intracranially, intravaginally or intratumorally.

In another embodiment, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In accordance with this embodiment, the compositions of the present invention comprise, in addition to the active compound and the inert carrier or diluent, a hard gelating capsule.

In another embodiment, the pharmaceutical compositions are administered by intravenous, intra-arterial, or intramuscular injection of a liquid preparation. Suitable liquid formulations include solutions, suspensions, dispersions, emulsions, oils and the like. In one embodiment, the pharmaceutical compositions are administered intravenously and are thus formulated in a form suitable for intravenous administration. In another embodiment, the pharmaceutical compositions are administered intraarterially and are thus formulated in a form suitable for intra-arterial administration. In another embodiment, the pharmaceutical compositions are administered intramuscularly and are thus formulated in a form suitable for intramuscular administration.

In another embodiment, the pharmaceutical compositions are administered topically to body surfaces and are thus formulated in a form suitable for topical administration. Suitable topical formulations include gels, ointments, creams, lotions, drops and the like.

In another embodiment, the pharmaceutical compositions are administered as a suppository, for example a rectal suppository or a urethral suppository. Further, in another embodiment, the pharmaceutical compositions are administered by subcutaneous implantation of a pellet. In a further embodiment, the pellet provides for controlled release of composition over a period of time.

In another embodiment, the active compound is delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intra-arterial, or intra-muscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In another embodiment, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

In one embodiment, the pharmaceutical compositions provided herein are controlled-release compositions, i.e. compositions in which the composition is released over a period of time after administration. Controlled- or sustained-release compositions include formulation in lipophilic depots (e.g. fatty acids, waxes, oils). In another embodiment, the composition is an immediate-release composition, i.e a composition in which all of the active compound is released immediately after administration.

In another embodiment, the pharmaceutical composition is delivered in a controlled release system. In another embodiment, the agent is administered using intravenous infusion, an implantable osmotic pump, a transdermal patch, liposomes, or other modes of administration. In another embodiment, a pump is used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials are used. In yet another embodiment, a controlled release system is placed in proximity to the therapeutic target. i.e., the brain, thus requiring only a fraction of the systemic dose (see, e.g., Goodson, in Medical Applications of Controlled Release, supra, vol. 2, pp. 115-138 (1984). Other controlled-release systems are discussed in the review by Langer (Science 249: 1527-1533 (1990).

The compositions also include, in another embodiment, incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

In another embodiment, the active ingredient is administered as a particulate composition coated with polymers (e.g. poloxamers or poloxamines) and the compound coupled to antibodies directed against tissue-specific receptors, ligands or antigens or coupled to ligands of tissue-specific receptors.

The preparation of pharmaceutical compositions that contain an active component, for example by mixing, granulating, or tablet-forming processes, is well understood in the art. The active therapeutic ingredient is often mixed with excipients that are pharmaceutically acceptable and compatible with the active ingredient. For oral administration, the active compound is mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the active compound is converted into a solution, suspension, or emulsion, if desired with the substances customary and suitable for this purpose, for example, solubilizers or other substances.

In another embodiment, the term "administering" refers to bringing a subject in contact with an active compound of the present invention. In another embodiment, administration can be accomplished in vitro, i.e. in a test tube, or in vivo, i.e. in cells or tissues of living organisms, for example humans.

EXPERIMENTAL DETAILS SECTION

Example 1

Mutation of Amino Acid 136 of VMAT 1 Correlates with BPD Materials and Experimental Methods Participants and Diagnoses 585 unrelated Bipolar Disorder (BPD) type I patients participated in this study. Patients were collected at centers participating in the National Institute of Mental Health (NIMH) Genetics Initiative on BPD and carried a diagnosis of BPD type I, defined by DSM-IV-criteria: The key criterion for admission of a family to the study was a diagnosis of BPD type I in two or more siblings. Background and detailed methodology for the NIMH Genetics Initiative are described in Dick D et al, Am J Hum Genet 73: 107-114, 2003). All subjects were assessed with the Diagnostic Instrument for Genetic Studies (Numberger J et al Arch Gen Psychiatry 51(11): 849-59, 1994). Family history information was obtained through the Family Interview for Genetic Studies (FIGS), and medical records were requested. Final best estimate diagnosis was made using all available information including medical records, information from relatives, and the DIGS interview, by two independent senior diagnosticians adhering to DSM-IV criteria. The patient group consisted of 38% males and 62% females. The average age at recruitment was 41.6 years. Psychotic symptoms were present in 66% of the probands at some point during their illness. Psychosis was defined as presence of auditory/visual hallucinations and/or paranoid or bizarre delusions.

The control subjects comprised 563 unrelated healthy individuals with no history of psychiatric or chronic neurological disease. The control group consisted of 51% males and 49% females with an average age of 38.5 years at recruitment. All cases and controls were of European descent. Informed consent was obtained from all individuals in accordance with Institutional Review Board (IRB) procedures DNA Analyses The VMAT1/SLC18A1 gene encodes 525 amino acids and consists of 16 exons spanning 38346 base pairs (bp). Review of the public database, the Celera database and the literature revealed 13 non-synonymous and 10 synonymous single nucleotide polymorphism (SNP) in the coding region of the SLC18A1 gene and at least 147 non-coding SNPs (Accession #NM 003053). SNPs for genotyping were chosen based on availability of Applied Biosystems Inc. (ABI) SNP assays, location in the gene and allele frequencies. Genotyping of three non-synonymous SNPs (Thr4Pro, Thr98Ser, Thr136Ile) and four intronic SNPs across the VMAT1/SLC 18A1 gene were performed using the ABI "Assays-on-demand" (ABI, Foster City, Calif., USA) SNP genotyping assay®.

Three additional missense mutations (rs17092144/Gln11Arg; rs17840571/Arg140Gly; rs17092104/Leu392Val) were genotyped in a subset of patients (n=94) and controls (n=190). Genotyping failure rates for all markers were less then 1% for controls and probands. Accuracy of genotyping was ensured by independent genotyping of a subgroup of the sample at the University of Pennsylvania DNA Core Facility. Concordance rates were greater than 99.5%.

rs17092104, rs17840571, rs988713, rs2270641, rs2270637, rs1390938, rs2279709, rs3735835, rs1497020, is 6586897, rs7820517, rs1018079, rs903997, and rs3779671 were detected using ABI assay ID # RS17092104-106, RS17840571-114, C__8804626__10, RS2270641-161, C__2716008__1, C__8804621__1, C__2716007__1, C__2715981__1, C__2715947__1, C__2716000__10, C__2716022__10, C__8804594__10, C__8804602__10, and C__22273041__10, respectively.

Statistical Analyses

Genotypes and allele frequencies were compared between groups using Chi square contingency analysis. A two-tailed type I error rate of 5% was chosen for the analysis.

The sample size utilized had power to detect a disease association at a P value less than or equal to 0.05, assuming an odds ratio of 1.5 (98% for a log additive mode of inheritance, 92% for a dominant and 27% for a recessive mode of inheritance). Power analysis was performed using the Quanto program (Gauderman W, Am J Epidemiol 155: 478-84, 2002).

Linkage disequilibrium (LD) was calculated using the 21d program (Zapata C et al Ann Hum Genet 65: 395406, 2001) and the Cocaphase program (Dudbridge F, Genet Epidemiol 25: 115-21, 2003). Haplotype frequencies were estimated using the Cocaphase program.

Results

All genotype counts were in Hardy-Weinberg equilibrium. Genotype and allele frequencies for the study are depicted in Table 1. As depicted in Table 1, a polymorphism at the codon of amino acid 136 in the VMAT1 gene correlated with the presence of BPD, with Thr over-represented in the BPD patients and Ile over-represented in the BPD patients and Ile over-represented in the control group. (p=0.003; df=1; OR=1.34; 95% CI: 1.11-1.62). In addition, two other SNP in the VMAT1 gene were associated with disease: one SNP in the promoter region (SNP1, rs988713, −584A/G, p=0.005, df=1; OR=1.31; 95% CI: 1.09-1.59) and one intronic SNP (SNP6, rs3735835, p=0.038; df=1; OR=0.86; 95% CI: 07'-0.99). Haplotype analysis revealed a haplotype associated with a low susceptibility to BPD; statistical significance was of the same level as the single marker analysis (Table 2). Strong LD was observed in the 5' end of the gene, and there was perfect LD between markers SNP1 and SNP4 (Table 3).

These findings show that polymorphisms of VMAT1/SLC18A1 (e.g. in AA 136) can be used to predict a predisposition or susceptibility to BPD. The findings also show that one or more protein products of VMAT1/SLC18A1 plays an important role in the etiology of BPD.

TABLE 1

Genotype and Allele frequencies of variations in the VMAT1/SLC18A1 gene in total BPD type I patients. BPD type I patients with psychotic symptoms ("BPDI psy"), and controls. P values are P type-I error rates for comparison of genotype and allele frequencies between BPD type I patients and controls.

| Sample | | n | Genotype frequencies | | | P* | Allele Freq. | P* |
|---|---|---|---|---|---|---|---|---|
| | | | A/A | A/G | G/G | | f(A) | |
| SNP1 | BP I | 585 | 0.591 | 0.366 | 0.043 | 0.015 | 0.774 | 0.005 |
| rs988713 | BP I psy | 392 | 0.584 | 0.367 | 0.048 | 0.085 | 0.768 | 0.029 |
| | Controls | 560 | 0.518 | 0.411 | 0.071 | | 0.723 | |
| | | | T/T | T/P | P/P | | f(Thr) | |
| SNP2 | BP I | 581 | 0.418 | 0.449 | 0.133 | 0.848 | 0.643 | 0.623 |
| rs2270641 | BP I psy | 390 | 0.397 | 0.469 | 0.133 | 0.642 | 0.632 | 0.356 |
| Thr4Pro | Controls | 560 | 0.427 | 0.452 | 0.121 | | 0.653 | |
| | | | T/T | T/S | S/S | | f(Thr) | |
| SNP3 | BP I | 584 | 0.635 | 0.317 | 0.048 | 0.633 | 0.794 | 0.415 |
| rs2270637 | BP I psy | 391 | 0.657 | 0.299 | 0.043 | 0.847 | 0.807 | 0.984 |
| Thr98Ser | Controls | 563 | 0.652 | 0.311 | 0.037 | | 0.807 | |

TABLE 1-continued

Genotype and Allele frequencies of variations in the VMAT1/SLC18A1 gene in total BPD type I patients. BPD type I patients with psychotic symptoms ("BPDI psy"), and controls. P values are P type-I error rates for comparison of genotype and allele frequencies between BPD type I patients and controls.

| Sample | | n | Genotype frequencies | | | P* | Allele Freq. | P* |
|---|---|---|---|---|---|---|---|---|
| | | | T/T | T/I | I/I | | f(Thr) | |
| SNP4 rs1390938 Thr136Ile | BP I | 580 | 0.597 | 0.360 | 0.043 | 0.009 | 0.777 | 0.003 |
| | BP I psy | 389 | 0.589 | 0.362 | 0.049 | 0.063 | 0.770 | 0.020 |
| | Controls | 560 | 0.518 | 0.409 | 0.073 | | 0.722 | |
| | | | C/C | C/A | A/A | | f(C) | |
| SNP5 rs2279709 | BP I | 585 | 0.330 | 0.484 | 0.186 | 0.271 | 0.572 | 0.127 |
| | BP I psy | 392 | 0.332 | 0.482 | 0.186 | 0.322 | 0.573 | 0.159 |
| | Controls | 561 | 0.287 | 0.506 | 0.207 | | 0.540 | |
| | | | G/G | G/C | C/C | | f(G) | |
| SNP6 rs3735835 | BP I | 585 | 0.287 | 0.480 | 0.232 | 0.069 | 0.527 | 0.038 |
| | BP I psy | 392 | 0.270 | 0.503 | 0.227 | 0.100 | 0.522 | 0.035 |
| | Controls | 561 | 0.319 | 0.503 | 0.178 | | 0.570 | |
| | | | A/A | A/G | G/G | | f(A) | |
| SNP7 rs1497020 | BP I | 583 | 0.504 | 0.417 | 0.079 | 0.100 | 0.713 | 0.205 |
| | BP I psy | 391 | 0.496 | 0.417 | 0.087 | 0.323 | 0.705 | 0.450 |
| | Controls | 560 | 0.493 | 0.391 | 0.116 | | 0.688 | |

Example 2

Specific VMAT1 Haplotypes Corelate with BPD

Haplotype analysis revealed that the G-Thr-Thr-Ile-A-G haplotype was more common in the controls (28%) versus in BPD patients (22%). This terminology refers to the polymorphism at SNP 1-6, respectively.

The findings of the present Example show that VMAT1 haplotypes of the present invention can be used to determine the predisposition or susceptibility of a subject to a mood disorder.

TABLE 2

Analysis of common haplotypes in the VMAT1/SLC18A1 gene. Haplotypes of SNPs 1-6 of Table 1 are depicted.

| Haplotype | # patients/ Frequency | # control subjects/ Frequency | OR | chisq | p |
|---|---|---|---|---|---|
| A-Thr-Thr-Thr-A-G | 113/0.102 | 108/0.100 | 1 | 0.031 | 0.858 |
| A-Thr-Thr-Thr-A-C | 114/0.103 | 89/0.081 | 1.232 | 2.945 | 0.086 |
| A-Thr-Ser-Thr-C-G | 225/0.203 | 206/0.190 | 1.047 | 0.621 | 0.430 |
| A-Pro-Thr-Thr-C-C | 401/0.363 | 376/0.347 | 1.022 | 0.589 | 0.442 |
| G-Thr-Thr-Ile-A-G | 251/0.227 | 303/0.280 | 0.793 | 8.023 | 0.004 |

TABLE 3

Linkage disequilibrium measures across the VMAT1/SLC18A1 gene.

| | | SNP1 | SNP2 | SNP3 | SNP4 | SNP5 | SNP6 | SNP7 |
|---|---|---|---|---|---|---|---|---|
| rs988713 | SNP1 | — | 1.00 | 1.00 | 1.00 | 1.00 | 1.00 | 0.46 |
| rs2270641 | SNP2 | 0.18 | — | 1.00 | 1.00 | 1.00 | 1.00 | 0.49 |
| rs2270637 | SNP3 | 0.08 | 0.13 | — | 1.00 | 1.00 | 1.00 | 0.38 |
| rs1390938 | SNP4 | 1.00 | 0.18 | 0.08 | — | 1.00 | 1.00 | 0.45 |
| rs2279709 | SNP5 | 0.42 | 0.43 | 0.19 | 0.42 | — | 0.53 | 0.42 |
| rs3735835 | SNP6 | 0.27 | 0.65 | 0.20 | 0.27 | 0.19 | — | 0.56 |
| rs1497020 | SNP7 | 0.16 | 0.05 | 0.01 | 0.15 | 0.09 | 0.11 | — |

Example 3

Polymorphisms in VMAT1 are Associated with Schizophrenia Materials and Experimental Methods Subjects Sixty two unrelated SZ patients participated in this study. Patients were collected at centers participating in the National Institute of Mental Health (NIMH) Genetics initiative for SZ (first wave) and carried a diagnosis of SZ as defined by DSM-IV criteria. All subjects were assessed with the Diagnostic Instrument for Genetic Studies. Family history information was obtained through the Family Interview for Genetic Studies (FIGS), and medical records were requested. Final best estimate diagnosis was made using all available information including medical records, information from relatives, and the DIGS interview, by two independent senior diagnosticians adhering to DSM-IV criteria. The control subjects comprised 188 unrelated healthy individuals with no history of psychiatric or chronic neurological disease. All patients and controls subjects were of European descent. Informed consent was obtained from all individuals, in accordance with Institutional Review Board (IRB) procedures.

DNA Analyses

The VMAT1/SLC18A1 gene encodes a protein of 525 amino acids, and consists of 16 exons spanning 38,346 bp (GenBank Accession # NM 003053). Genotyping of four non-synonymous SNPs (Thr4Pro, Thr98Ser, Thr136Ile, Val392Leu) and two intronic SNPs across the VMAT1/SLC18A1 gene was performed using the Applied Biosystems Inc. (ABI) "Assays-on-demand"® (ABI, Foster City, Calif., USA) SNP genotyping assay, as per the manufacturer's protocol (SNP1=rs988713; SNP2=rs2270641 (Thr4Pro); SNP3=C2716008/rs2270637 (Thr98Ser); SNP4=rs1390938 (Thr136Ile); SNP5=rs2279709; SNP8=rs17092104 [Leu392Val]).

Statistical Analyses

Genotypes and allele frequencies were compared between groups using Chi square contingency analysis. A two-tailed type I error rate of 5% was chosen for the analysis. Linkage disequilibrium (LD) and haplotype frequencies were estimated using the COCAPHASE program (F Dudbridge (2003), "Pedigree disequilibrium tests for multilocus haplotypes," Genetic Epidemiology, 25:115-121). The COCAPHASE program uses standard unconditional logistic regression analysis. Haplotype analysis was performed using a 6-marker window. Rare haplotypes were excluded from analysis.

RESULTS

All genotype counts were in Hardy-Weinberg equilibrium. Strong LD was observed in the 5' end of the gene, and perfect LD was observed between markers SNP1 and SNP4 (Table 4).

Single marker analysis (Table 5) revealed that the frequency of the minor allele of the Thr4Pro polymorphism was significantly increased in SZ patients as compared to controls (p=0.0140; df=1; OR: 1.69; 95%-CI: 1.11-2.57). In addition, the genotypic distribution differed significantly between patients and controls (p=0.003). Moreover, the frequency of 4Pro homozygotes (24%) was significantly increased in the SZ patients as compared to controls (8%) (p=0.0006, df=1; OR: 3.74; 95%-CI: 1.703-8.21). Homozygosity for the minor allele substantially increased the risk for disease; the increased odds ratio was 3.74; 95%-CI: 1.703-8.21.

Haplotype analysis (Table 6) revealed statistical significance for an individual haplotype, 1-2-1-1-1-1 (p=0.013); after permutation correction, the global p value was 0.07. This terminology refers to the polymorphisms of SNP 1-5 and 8, respectively. "1" and "2" refer to the major allele (1) or minor allele (2) at each location; e.g. "1-2-1-1-1-1" refers to A-Pro-Thr-Thr-C-Val.

Thus, the Thr4Pro polymorphism is a marker for schizophrenia. In addition, the 1-2-1-1-1-1(A-Pro-Thr-Thr-C-Val) haplotype correlates with schizophrenia.

TABLE 4

Linkage Disequilibrium measures across the VMAT1 gene

|  |  | SNP1 | SNP2 | SNP3 | SNP4 | SNP5 | SNP6 |
|---|---|---|---|---|---|---|---|
| rs988713 | SNP1 | — | 1.00 | 1.00 | 1.00 | 1.00 | 1.00 |
| rs2270641 | SNP2 | 0.17 | — | 0.84 | 0.96 | 0.98 | 0.86 |
| rs2270637 | SNP3 | 0.07 | 0.08 | — | 1.00 | 1.00 | 0.17 |
| rs1390938 | SNP4 | 0.99 | 0.16 | 0.07 | — | 1.00 | 1.00 |
| rs2279709 | SNP5 | 0.36 | 0.45 | 0.19 | 0.36 | — | 0.19 |
| rs17092104 | SNP8 | 0.04 | 0.05 | 0.01 | 0.04 | 0.01 | — |

Note: D' values are given above the diagonal, and $r^2$ values are given below the diagonal.

TABLE 5

Genotype and Allele frequencies of variations in the VMAT1/SLC18A1 gene.

| SNP |  | Sample | n | Genotype frequencies | | | P*[a] | Allele Frequencies | P*[b] |
|---|---|---|---|---|---|---|---|---|---|
| SNP1 | rs988713 |  |  | A/A | A/G | G/G |  | f(G) |  |
|  |  | SZ | 61 | 0.623 | 0.328 | 0.049 | 0.455 | 0.213 | 0.221 |
|  |  | Ctrls | 186 | 0.532 | 0.398 | 0.070 |  | 0.269 |  |
| SNP2 | rs2270641 |  |  | Thr/Thr | Thr/Pro | Pro/Pro |  | f(Pro) |  |
|  | Thr4Pro | SZ | 61 | 0.377 | 0.377 | 0.246 | 0.003 | 0.434 | 0.014 |
|  |  | Ctrls | 187 | 0.455 | 0.465 | 0.080 |  | 0.313 |  |
| SNP3 | rs2270637 |  |  | Thr/Thr | Thr/Ser | Ser/Ser |  | f(Ser) |  |
|  | Thr98Ser | SZ | 62 | 0.677 | 0.290 | 0.032 | 0.991 | 0.177 | 0.912 |
|  |  | Ctrls | 187 | 0.668 | 0.299 | 0.032 |  | 0.182 |  |
| SNP4 | rs1390938 |  |  | Thr/Thr | Thr/Ile | Ile/Ile |  | f(Ile) |  |
|  | Thr136Ile | SZ | 62 | 0.613 | 0.339 | 0.048 | 0.517 | 0.218 | 0.248 |
|  |  | Ctrls | 187 | 0.535 | 0.390 | 0.075 |  | 0.270 |  |
| SNP5 | rs2279709 |  |  | C/C | C/A | A/A |  | f(A) |  |
|  |  | SZ | 61 | 0.426 | 0.344 | 0.230 | 0.044 | 0.402 | 0.059 |
|  |  | Ctrls | 188 | 0.261 | 0.479 | 0.261 |  | 0.500 |  |
| SNP8 | rs17092104 |  |  | Val/Val | Val/Leu | Leu/Leu |  | f(Leu) |  |
|  | Val392Leu | SZ | 62 | 0.774 | 0.226 | 0.000 | 0.340 | 0.113 | 0.901 |
|  |  | Ctrls | 188 | 0.793 | 0.181 | 0.027 |  | 0.117 |  |

*denotes type-I error rates for comparison of genotype[a] and allele[b] frequencies between schizophrenia patients and controls.

TABLE 6

Analysis of common haplotypes of SNP1-5 and 8 in the VMAT1 gene

| Haplotype | Case | freq | Control | freq | OR | chisq | p |
|---|---|---|---|---|---|---|---|
| 1-1-1-1-2-1 | 15 | 0.147 | 56 | 0.171 | 1 | 0.350 | 0.553 |
| 1-1-1-1-2-2 | 5 | 0.049 | 25 | 0.076 | 0.746 | 0.982 | 0.321 |
| 1-1-2-1-1-1 | 11 | 0.107 | 48 | 0.147 | 0.855 | 1.063 | 0.302 |
| 1-2-1-1-1-1 | 47 | 0.460 | 106 | 0.325 | 1.655 | 6.086 | 0.013 |
| 2-1-1-2-2-1 | 24 | 0.235 | 91 | 0.279 | 0.984 | 0.775 | 0.378 |

Example 4

VMAT1 and VMAT2 are Both Expressed in Human Brain Materials and Experimental Methods Expression Analyses Commercially available human brain cDNA was purchased from Clontech Laboratories, Inc. (amygdala, hippocampus, substantia nigra) and Invitrogen Corporation (adult frontal lobe, thalamus, fetal frontal lobe). Expression assays for VMAT1 and VMAT2 were chosen based on specificity after sequence alignment of both in RNAs (VMAT1: Hs_0091591, NM 003053, 2749 bp; VMAT2: Hs_00161858. NM 003054, 1898 bp). GAPDH was used as a normalizer (Hs 9999905). To avoid possible genomic DNA amplification, probes were designed to cross exon-exon junctions Real-time quantitative PCR using 2 nanograms (ng) of cDNA per reaction was performed using Applied Biosystems 7300 Sequence Detection System® as per the manufacturer's protocol, and control samples lacking template were included with each assay. Relative quantification was performed using the comparative CT method ($\Delta\Delta C_T$).

RESULTS

Real-time quantitative PCR expression analysis of human brain cDNA was used to determine VMAT1 and VMAT2 mRNA expression in various brain regions (FIG. 1). The highest levels of VMAT1 were observed in substantia nigra, followed by amygdala, hippocampus, thalamus, fetal frontal lobe and frontal lobe. VMAT2 expression was highest in substantia nigra.

These results show that VMAT1 plays a role in brain physiology. Thus, detection of VMAT1 polymorphisms has utility as a method for determining and predicting predisposition to neuro-psychiatric diseases and disorders. In addition, supplying functional VMAT1 protein to the brain (e.g. via gene therapy) can be used to treat neuro-psychiatric diseases and disorders.

Example 5

Refinement of Analysis to Identify Polymorphisms and Haplotypes Associated with Particular Psychosis Sub-Types The schizophrenic patient group is sub-divided into sub-types, such as paranoid schizophrenia, disorganized schizophrenia (Hebephrenic Schizophrenia), catatonic schizophrenia, residual schizophrenia, schizoaffective disorder, undifferentiated schizophrenia, persistent delusional disorders, psychotic affective disorders, dementia with psychotic symptoms, and delirium. Sequence data of VMAT1 and other VMAT genes is analyzed as described in the above. Examples to identify polymorphisms and haplotypes associated with particular schizophrenia subtypes. These polymorphisms and haplotypes are then used to design diagnostic tests, kits, and novel therapeutic protocols for the schizophrenia subtypes.

Example 6

Refinement of Diagnostic and Therapeutic Protocols for BPD According to Ethnic Background The VMAT1 sequence analysis of the above Examples is performed on individuals of non-European descent, in order to refine the diagnostic and treatment protocols according to ancestry or background.

Example 7

Identification of Additional Polymorphisms and Haplotypes Associated with Bpd, Schizophrenia, and Other Neuro-Psychiatric Diseases VMAT1 sequence analysis similar to that of the above Examples is performed using a family-based association design to identify additional polymorphisms and haplotypes associated with BPD, schizophrenia, and other neuro-psychiatric diseases and disorders.

---

What is claimed is:

1. A method of determining a predisposition or susceptibility of a human subject to bipolar disorder comprising
   a) determining a genotype of said subject for:
      i) a polymorphism in position −584 of the vesicular monamine transporter 1 (VMAT1) gene
      ii) a polymorphism in codon 4 of the VMAT1 gene
      iii) a polymorphism in codon 98 of the VMAT1 gene
      iv) a polymorphism in codon 136 of the VMAT1 gene
      v) a polymorphism at position 26 of SEQ ID NO: 9
      vi) polymorphism at position 26 of SEQ ID NO: 8
   b) detecting the G-Thr-Thr-Ile-A-G combination of alleles of said polymorphisms and
   c) correlating the presence of the combination of alleles with predisposition or susceptibility to bipolar disorder.

2. The method of claim 1, wherein said bipolar disorder is a bipolar disorder type I.

3. The method of claim 1, wherein the step of determining comprises a polymerase chain reaction.

4. A method of determining a predisposition or susceptibility of a human subject to schizophrenia comprising
   a) determining a genotype of said subject for:
      i) a polymorphism in position −584 of the vesicular monamine transporter 1 (VMAT1) gene
      ii) a polymorphism in codon 4 of the VMAT1 gene
      iii) a polymorphism in codon 98 of the VMAT1 gene
      iv) a polymorphism in codon 136 of the VMAT1 gene
      v) a polymorphism at position 26 of SEQ ID NO: 9
      vi) a polymorphism in codon 392 of the VMAT1 gene
   b) detecting the A-Pro-Thr-Thr-C-Val combination of alleles of said polymorphisms and
   c) correlating the presence of the combination of alleles with predisposition or susceptibility to schizophrenia.

5. The method of claim 4, wherein the step of determining comprises a polymerase chain reaction.

6. A method of identifying a combination of polymorphisms in the vesicular monamine transport 1 (VMAT1) gene predictive of a predisposition or susceptibility of a human subject to a mood disorder, comprising
   a) determining the genotypes of human subjects diagnosed as having a mood disorder and control subjects for said combination of polymorphisms in said VMAT1 gene
   b) comparing the prevalence of said genotype in said subjects diagnosed as having a mood disorder with said control subjects, and
   c) correlating said combination of polymorphisms with said mood disorder diagnosis, wherein said combination comprises polymorphisms selected from:
      i) a polymorphism in position −584 of the VMAT1 gene
      ii) a polymorphism in codon 4 of the VMAT1 gene
      iii) a polymorphism in codon 98 of the VMAT1 gene
      iv) a polymorphism in codon 136 of the VMAT1 gene
      v) a polymorphism at position 26 of SEQ ID NO: 9.

7. The method of claim 6, wherein said mood disorder is a bipolar disorder or a manic-depressive disorder.

8. The method of claim 6, wherein the step of determining comprises a polymerase chain reaction.

9. The method of claim 6, wherein said combination further comprises a polymorphism at position 26 of SEQ ID NO: 8.

10. A method of identifying a combination of polymorphisms in the vesicular monamine transport 1 (VMAT1) gene predictive of a predisposition or susceptibility of a human subject to schizophrenia, comprising
    a) determining the genotypes of human subjects diagnosed as having schizophrenia and control subjects for said combination of polymorphisms in said VMAT1 gene
    b) comparing the prevalence of said genotype in said subjects diagnosed as having schizophrenia with said control subjects, and
    c) correlating said combination of polymorphisms with schizophrenia diagnosis, wherein said combination comprises polymorphisms selected from:
        i) a polymorphism in position −584 of the VMAT1 gene
        ii) a polymorphism in codon 4 of the VMAT1 gene
        iii) a polymorphism in codon 98 of the VMAT1 gene
        iv) a polymorphism in codon 136 of the VMAT1 gene
        v) a polymorphism at position 26 of SEQ ID NO: 9.

11. The method of claim 10, wherein the step of determining comprises a polymerase chain reaction.

12. The method of claim 10, wherein said combination further comprises a polymorphism at position 26 of SEQ ID NO: 8.

* * * * *